United States Patent [19]

Pujado

[11] Patent Number: 4,797,133
[45] Date of Patent: Jan. 10, 1989

[54] PROCESS FOR RECOVERY OF BUTENE-1 FROM MIXED C4 HYDROCARBONS

[75] Inventor: Peter R. Pujado, Palatine, Ill.
[73] Assignee: UOP Inc., Des Plaines, Ill.
[21] Appl. No.: 946,999
[22] Filed: Dec. 29, 1986
[51] Int. Cl.$^4$ .............................................. C10L 1/02
[52] U.S. Cl. ........................................ 44/53; 44/50; 568/697
[58] Field of Search ...................... 44/53, 50; 568/697

[56] References Cited

U.S. PATENT DOCUMENTS

| | | | |
|---|---|---|---|
| 3,726,942 | 4/1973 | Louder | 260/683.6 |
| 3,912,463 | 10/1975 | Kozolowski | 44/56 |
| 4,193,770 | 3/1980 | Chase | 44/53 X |
| 4,219,678 | 8/1980 | Obenaus et al. | 568/697 |
| 4,282,389 | 8/1981 | Droste et al. | 568/697 |
| 4,324,924 | 4/1982 | Torck et al. | 568/697 |
| 4,334,890 | 6/1982 | Kochar | 44/53 |
| 4,413,150 | 11/1983 | Briggs | 44/56 X |
| 4,513,153 | 4/1985 | Sandrin | 568/697 |
| 4,544,777 | 10/1985 | Hutson, Jr. et al. | 568/697 |

OTHER PUBLICATIONS

Herwig, J. et al., "New Low Energy Process for MIBE and TAME", *Hydrocarbon Processing*, pp. 86–88.
Obenaus, Fritz Dr., "Huls-Process: Methyl Tertiary Butylether", AIChe 85th National Meeting, Philadelphia, Jun. 4–8, 1978.
Stinson, Stephen C., "New Plants, Processes Set for Octane Booster", *C&EN*, Jun. 25, 1979, pp. 35–36.
Clementi, A. et al., "Upgrade C4's with MTBF Process", *Hydrocarbon Processing*, pp. 109–113.

*Primary Examiner*—William R. Dixon, Jr.
*Assistant Examiner*—James M. Hunter, Jr.
*Attorney, Agent, or Firm*—Thomas K. McBride; John F. Spears, Jr.

[57] ABSTRACT

A process is disclosed for the recovery of butene-1 from a mixed C4 feed stream which also contains isobutylene, butene-2, isobutane and normal butane. The C4 feed stream is passed through an etherification reaction zone wherein isobutylene is selectively converted to an ether. The effluent of the etherification reaction zone is fractionated to produce a first stream comprising the product ether and C4 hydrocarbons and a second stream comprising isobutane and butene-1. The second stream is then separated to yield the butene-1. The first stream is preferably utilized in motor fuel production as by direct blending into a naphtha boiling material or by passage into an alkylation zone.

24 Claims, 1 Drawing Sheet

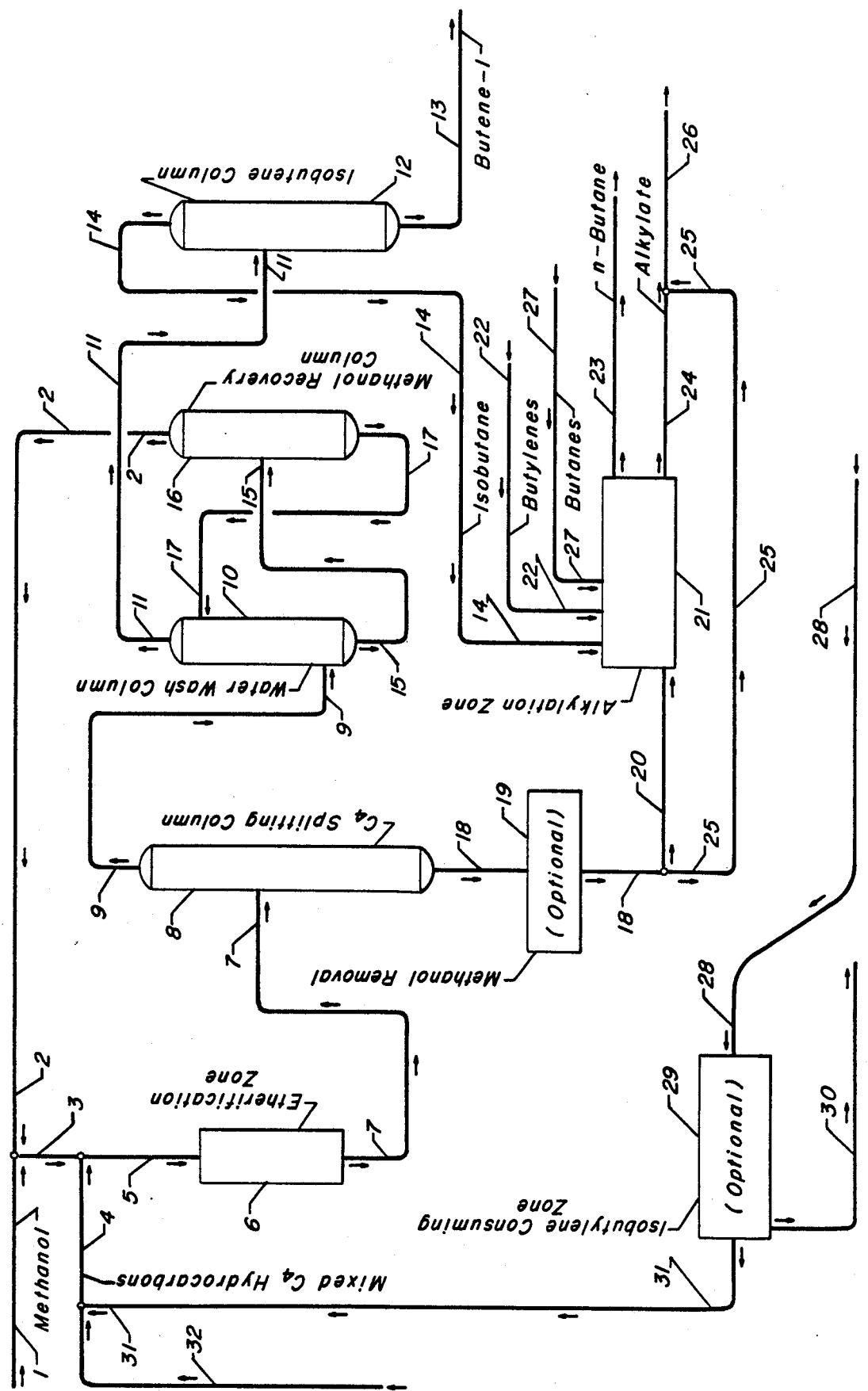

PROCESS FOR RECOVERY OF BUTENE-1 FROM MIXED C4 HYDROCARBONS

FIELD OF THE INVENTION

The invention is a process for the recovery of butene-1 from a mixed phase $C_4$ feedstream. The subject invention is directly concerned with the use of an etherification reaction to selectively remove isobutylene from a mixed $C_4$ feedstream to allow the commercially practical separation of butene-1 from the remaining $C_4$ hydrocarbons by fractional distillation. The invention is specifically directed to the passage of an isobutylene depleted $C_4$ feedstream into the etherification zone and to the subsequent fractional distillation of the effluent of the etherification zone into a first stream containing butene-1 and a second stream containing the product ether and other $C_4$ hydrocarbons present in the $C_4$ feedstream.

PRIOR ART

The production of methyl tertiary butyl ether (MTBE) by the reaction of isobutylene with methanol is believed to be highly relevant to the subject invention. Information about this etherification process and a simplified flow diagram is presented in the article starting at page 86 of the June 1984 edition of *Hydrocarbon Processing*. A description of a similar etherification process is presented in the paper presented at the AIChe 85th National Meeting, Jun. 4-8, 1978 by Fritz Obenaus and Wilhelm Droste, entitled, "Huls-Process: Methyl Tertiary Butyl Ether". This process was also described in the article at page 35 of the Jun. 25, 1979 edition of *Chemical and Engineering News*.

U.S. Pat. Nos. 4,219,678 and 4,282,389 are also believed pertinent for their teaching in regard to the operation of the etherification zone, possible feedstreams to this zone, and the methods which can be employed in processing the effluent stream removed from the etherification reaction zone. These references illustrate that it is known to pass the etherification reaction zone effluent stream into a water wash column for the recovery of methanol, followed by the recovery of methanol from the water. The recycling of methanol to the reaction zone is also disclosed in these references.

The non-patent references indicate that the etherification reaction zone effluent stream may be fractionated in different flow schemes to yield different product streams of MTBE purity. It is believed relevant that in one of these alternatives the entire effluent of the reaction zone itself may be withdrawn for use as a gasoline blending stream. However, it is believed that heretofore when the effluent of the etherification reaction zone has been passed into a fractionation column in which $C_4$ hydrocarbons are removed overhead that essentially all of the $C_4$ hydrocarbons have been removed in the net overhead stream of the fractionation column. That is, it is believed that heretofore no substantial part of the $C_4$ hydrocarbons present in the etherification reaction zone effluent stream have been removed as a portion of the net bottoms stream of the $C_4$ column or debutanizer which receives the etherification reactor effluent.

U.S. Pat. No. 4,324,924 issued to B. Torck et al. is pertinent for its teaching of a two-stage etherification process for the production of MTBE. In this process it is indicated that the MTBE produced in the first reaction zone may be separated from the effluent of the first reaction zone prior to the passage of the remaining $C_4$ hydrocarbons and methanol into a second etherification reaction zone. In this manner the feedstream to the second etherification reaction zone would be an isobutylene depleted feedstream such as employed in the preferred embodiment of the subject process.

It is known in the art that an etherification process may be employed to selectively consume isobutylene as one step in an overall process which yields butene-1. For instance, one possible flow is presented as FIG. 4 of the AIChe meeting paper referred to above. The article starting at page 109 of the December 1975 issue of *Hydrocarbon Processing*. is believed pertinent for its discussion of the utilization of an MTBE process in the recovery of pure $C_4$ hydrocarbon streams including 1-butene. This paper indicates that butene-2 can be separated by conventional distillation from a $C_4$ feedstream but the separation of isobutylenes and butene-1 is almost impossible in this manner. This paper also indicates that different processes are available for this separation as for example the cold acid ($H_2SO_4$) extraction process for obtaining isobutylene and the selective adsorption processes for butene-1 and butene-2 separation. The reference in FIG. 2 gives a block diagram indicating the use of an MTBE etherification zone to remove isobutylene upstream of a butene-1 recovery zone. U.S. Pat. No. 4,513,153 issued to R. Sandrin is believed pertinent for its teaching of the removal of isobutylene from a $C_4$ feedstock through the production of tertiary butyl alkyl ethers prior to the recovery of butene-1 at high purity by extractive distillation.

U.S. Pat. No. 3,726,942 issued to K. E. Louder and U.S. Pat. No. 4,544,777 issued to T. Hudson, Jr. et al. are believed pertinent for their teaching that an etherification zone producing MTBE may be integrated with a $C_4$ alkylation zone producing motor fuel alkylate. In these processes, the unconverted hydrocarbons discharged from the MTBE reaction zone and separated therefrom by fractional distillation are passed into an alkylation zone wherein, as in the preferred embodiment of the subject invention, HF is employed as a catalyst.

U.S. patent application Ser. No. 764,707 filed 8-12-85 by T. Imai et al. teaches the beneficial presence of MTBE in an HF alkylation reaction zone. The MTBE and the HF combine to form a single liquid phase catalyst which produces a higher octane number product than is achieved through the use of HF alone.

BRIEF SUMMARY OF THE INVENTION

The invention provides a method to recover high purity butene-1 from a mixed $C_4$ feedstream. The invention also provides an ether-containing second product stream which may be directly blended with a motor fuel stock or which may be passed into an alkylation zone. The invention is specifically directed to processing mixed $C_4$ feedstreams containing a relatively low concentration of isobutylene, and is distinguished by the fractional distillation of the etherification zone effluent stream into an overhead stream comprising butene-1 and at least one other $C_4$ hydrocarbon and a net bottoms stream comprising the product ether and containing at least 10 percent $C_4$ hydrocarbons.

One broad embodiment of the invention may be characterized as a process for the production of butene-1, which process comprises the steps of contacting a mixed $C_4$ feedstream comprising isobutylene, isobutane, normal butane and butene-1 and an alcohol with an etherification catalyst maintained at etherification promoting conditions in a reaction zone, and producing a reaction zone effluent stream comprising the alcohol, normal butane, butene-1, isobutane and a $C_4$-plus ether; separating the reaction zone effluent stream in a first fractionation zone into a net overhead stream comprising butene-1 and isobutane and a net bottoms stream comprising normal butane, butene-2 and the ether, with the net bottoms stream having a hydrocarbon concentration above 10 mole percent; recovering the net bottoms stream as a first product stream; and separating the net overhead stream in a second fractionation zone into a second product stream rich in isobutane and a third product stream rich in butene-1.

BRIEF DESCRIPTION OF THE DRAWING

The drawing is a simplified process flow diagram illustrating the passage of a mixed $C_4$ hydrocarbon stream of line 4 through an etherification zone 6 and the subsequent separation of the etherification zone effluent into a butene-1 containing stream of line 9 and the $C_4$ hydrocarbon rich stream of line 18 which contains the MTBE produced in the etherification zone.

DETAILED DESCRIPTION

Methyl tertiary butyl ether (MTBE) is being used increasingly as an octane booster in gasolines. The use of other ethers such as tertiary amyl ethers (TAME) as a gasoline additive has also been taught. Ethers are also important industrial chemicals useful by themselves or as intermediates or feed materials in the production of other petrochemicals. As octane boosters the ethers are being employed to satisfy the octane demands of modern automotive engines and to counteract the effects of eliminating lead containing compounds from gasoline blending pools in the production of lead free gasoline. The straight chain butenes are useful as feedstocks to polymerization processes. Butene-1 is used as a comonomer in the production of linear low density polyethylene (LLDPE). It is also used in the production of polybutene-1. Of the normal butenes, butene-1 is the more highly prized feedstock in such applications. Polybutene-1 has certain qualities giving it advantages over such plastics as polyethylenes and polyvinylchloride in some instances.

It is an objective of the subject invention to provide a process which yields a high-quality butene-1 product stream. It is a further objective of the subject invention to provide a process for recovering butene-1 from an isobutylene depleted mixed $C_4$ feedstream. It is a further objective of the subject invention to provide a process which produces an ether-containing product stream suitable for use as a gasoline-blending component and also produces a butene-1 product stream.

The feedstream to the subject process is a mixed $C_4$ feedstream. The feedstream may contain other hydrocarbons but preferably this feedstream will contain less than 10 mole percent total $C_5+$ and $C_3-$ hydrocarbons. That is, preferably over 90 mole percent of the hydrocarbons in the feedstream will be $C_4$ hydrocarbons. The feedstream may contain higher concentrations of $C_5$ hydrocarbons as, for instance, when it is desired to perhaps coproduce methyl tertiary butyl ether and tertiary amyl ether. The feedstreams in any instance must contain a mixture of normal butenes and isobutylene. The feedstream therefore must contain butene-1, butene-2, and isobutylene. These olefinic hydrocarbons are normally produced in commercial quantities by a cracking process such as thermal cracking or fluidized catalytic cracking. In the latter instance the $C_4$ olefins are a valuable by-product of the FCC process typically operated to produce gasoline and other distillates in a petroleum refinery. Another potential source of the feedstream is a catalytic dehydrogenation zone operating on a $C_4$ feedstream. The feedstream will also contain the saturated $C_4$ hydrocarbons normal butane and isobutane. If appreciable amounts of $C_5$ hydrocarbons are present in the feedstream, the feedstream will normally contain the equivalent mixture of pentenes and pentanes. Many feedstreams will also contain butadiene if they have not been subjected to treatment for the removal of this material. Butadiene present in the feedstream will normally be removed at some point within the process as described herein.

The subject process can be operated utilizing a wide variety of feedstreams. However, it is preferred that an "isobutylene-depleted" $C_4$ feedstream be charged to the process. As used herein, the term "isobutylene-depleted" is intended to indicate a feedstream which contains less than about 5 mole percent isobutylene and preferably contains less than about 2.5 mole percent isobutylene. Such low isobutylene content feedstreams may be the result of the source of the $C_4$ feedstream producing a distribution of olefins skewed to the production of normal butenes. However, it is believed that the normal source of the isobutylene-depleted feedstream will be an effluent stream discharged by a isobutylene-consuming zone.

As used herein, the term "isobutylene-consuming zone" is intended to broadly encompass separation or conversion zones which with a high degree of selectivity result in the removal of isobutylene from a charge stream fed to that zone. Examples of such isobutylene-consuming zones are the previously referred to cold acid extraction process, adsorptive separation, and reaction zones including hydration zones used to produce alcohol or etherification zones. An example of such a sequence of processing zones is presented in U.S. Pat. No. 4,423,251 which is incorporated herein by reference. In this reference, a mixed $C_4$ charge stream enters the process. In one embodiment a portion of the charge stream is passed through a hydration zone for the production of tertiary butyl alcohol, with the $C_4$ hydrocarbons recovered from the hydration zone effluent stream being admixed with the portion of the charge stream which is not charged to the hydration zone. The recombined charge stream is then passed into an etherification zone. The recombined charge stream will have a lower concentration of isobutylene than the original mixed $C_4$ charge stream.

The feedstream to the process should contain at least 12 mole percent butene-1. The feedstream may contain as much as 40–50 mole percent if the $C_4$ hydrocarbons originate from a steam cracking unit and have been fractionated. If the feedstream originates from a fluidized catalytic cracking (FCC) unit, it will contain a sizable amount of isobutane. The advantages of the subject invention increase with higher butene-1 concentrations.

To achieve the objectives set out above, the $C_4$ feedstream is passed into an etherification zone and contacted with a suitable etherification catalyst in the presence of an alcohol. This produces an etherification reaction zone effluent stream comprising ether, any residual alcohol and the remaining unconverted $C_4$ hydrocarbons. This reaction zone effluent stream is passed into a fractionation zone which preferably comprises a single fractional distillation column. The reaction zone effluent stream is therein separated into an overhead stream containing essentially all, that is at least 95 mole percent, of the butene-1 present in the reaction zone effluent stream and a net bottoms stream comprising substantially all of the ether present in the reaction zone effluent stream and having a substantial concentration of $C_4$ hydrocarbons. The net bottoms stream should contain at least about 10 mole percent $C_4$ hydrocarbons. Preferably, the net bottoms stream withdrawn from the first fractionation zone contains over about 25 mole percent $C_4$ hydrocarbons. It is highly preferred that the net bottoms stream removed from the first fractionation zone contains over 50 mole percent $C_4$ hydrocarbons.

The drawing illustrates several different embodiments of the subject process. These different embodiments are in addition to the variations possible in feedstocks, reaction zone configurations and separation techniques as set out elsewhere. Several variations illustrated on the drawing employ optional zones, and the drawing therefore also illustrates process flows which are optional. Accordingly, the drawing is not intended to limit the scope of the invention to the embodiments shown. Referring now to the drawing, a mixed $C_4$ feedstream enters the process through line 32. In this basic embodiment of the invention, the $C_4$ feedstream continues through line 4 and is admixed with a feedstream of methanol carried by lines 1 and 3. The admixture of methanol and $C_4$ hydrocarbons then passes through line 5 into an etherification zone 6. The etherification zone is preferably operated at the conditions set out herein and contains a resin-type catalyst as described herein.

The action of the catalyst on the isobutylene and the methanol results in the production of methyl tertiary butyl ether by the reaction of methanol and isobutylene. There is thereby formed a reaction zone effluent stream carried by line 7 which comprises residual methanol, MTBE, and the $C_4$ hydrocarbons which are not consumed in the etherification reaction. The admixture of these materials is passed into a $C_4$ splitting column 8. This column is operated under conditions which effect the separation of the entering materials into a net overhead stream removed through line 9 which comprises methanol, isobutane and butene-1 and a net bottoms stream which comprises MTBE, normal butane and butene-2. Due to the imprecise separation of some intermediate boiling compounds which is obtained in a commercial splitting column, the bottoms stream may also contain some methanol and small amounts of isobutane and butene-1. If the feedstream originates in an FCC unit, the net bottoms may contain a sizable amount, e.g. over 15 mole percent, isobutane.

The net overhead stream of the $C_4$ splitting column 8 is passed through line 9 into the bottom of a water wash column 10. In this column, the entering hydrocarbon stream is passed upward countercurrent to descending liquid phase water, passed into an upper portion of the water wash column through line 17. The multiple stages of contacting between the ascending hydrocarbons and the descending water result in the transfer of essentially all of the methanol present in the entering hydrocarbon stream to the aqueous stream. The aqueous stream is removed from the bottom of the water wash column through line 15 and passed into the methanol recovery column 16. The methanol recovery column is a fractional distillation column operated to split the entering materials into a net bttoms stream of high purity water which is returned to the water wash column through line 17 and a net overhead stream containing the methanol entering the recovery column via line 9. The net overhead stream is preferably recycled through line 2 to allow consumption of the methanol within the etherification zone. The methanol recovery column should be operated in a method to minimize the water content of the methanol recycle stream and to thereby avoid the production of tertiary butyl alcohol by reaction of water with isobutylene in the etherification zone.

The liquid phase material removed from the top of the water wash column 10 comprises an admixture of the $C_4$ hydrocarbons discharged overhead from the splitting column 8. This admixture is passed through line 11 into a second fractionation zone represented by the single fractional distillation column 12. The isobutane column 12 operates as a splitting column to separate the entering materials into a net bottoms stream withdrawn through line 13 and comprising high-purity butene-1 and a net overhead stream removed through line 14 and containing substantially all of the isobutane which enters column 12. Both the net overhead and bottom streams of column 12 may be withdrawn from the process as product streams. Not shown on the drawing is the overhead condensing system of isobutane column 12 which will normally contain a condensing means and a liquid-liquid separation means which allows a water stream to be removed. The water phase results from the hydrocarbons of line 11 being saturated with the wash water.

The net bottoms stream of the $C_4$ splitting column 8 may be passed through an optional methanol removal zone 19 if the net bottoms stream contains methanol and it is desired to remove the methanol. It is normally not desired to allow methanol to enter an HF alkylation zone since it accumulates in the HF and is very difficult to remove. The methanol may also result in undesired water product in the alkylation zone. If the entire net bottoms stream is destined for usage as a gasoline-blending component, it may be entirely acceptable to allow methanol to remain in the bottoms stream. For instance, if the entire bottoms stream of line 18 is passed into line 25 for admixture with an alkylation zone product stream (motor fuel precursor) carried by line 24 it may not be necessary to remove methanol from the bottoms stream.

In one limited embodiment of the invention, all or a portion of the net bottoms stream of the splitting column 8 is passed through line 20 into an alkylation zone 21. Preferably, the alkylation zone utilizes HF as at least one component of a liquid phase catalyst system. It has been found that a catalyst system comprising an admixture of HF and less than about 15 mole percent MTBE results in an octane number increase in the product alkylate as compared to the usage of an MTBE-free HF catalyst system when butene-1 is charged to the alkylation zone. The MTBE present in the material of stream 20 would therefore be employed to maintain the MTBE concentration desired in the alkylation zone, with excess material being discharged with the alkylate. In the alkylation zone 21, isobutane from line 14 or contained within the butane feedstream of line 27 combines with normal butenes such as butene-2 present in lines 22 and 20. This results in the production of $C_8$ branched chain hydrocarbons having a high octane number. The $C_8$ product hydrocarbons are discharged as an alkylate product stream in line 24, with the unreactive normal butane which enters the alkylation zone as in lines 20 and 27 being discharged from the alkylation zone in line 23. The butane stream of line 23 is produced in a fractionation column within the alkylation zone. Other streams such as a stream of propane may also be discharged from the alkylation zone through a line not shown. The alkylate may be removed directly from the process or may be admixed with the MTBE-containing $C_4$ hydrocarbon stream of line 25 and withdrawn as a admixture of gasoline-blending components through line 26.

In another embodiment of the invention, a mixed $C_4$ hydrocarbon stream is charged to an overall process through line 28. This mixed $C_4$ charge stream first passes into an isobutylene-consuming zone 29 where as by extraction or reaction as set out above, a portion of the isobutylene content of the original feedstream is removed from the charge stream. This may result in the production of a stream of isobutylene discharged from zone 29 through line 30 or a product stream of a petrochemical product such as MTBE or TBA discharged from zone 29 through line 30. The resultant isobutylene depleted $C_4$ stream discharged from the isobutylene-consuming zone is passed through lines 31 and 4 into the etherification zone 6. The isobutylene depleted stream of line 31 may optionally be augmented by $C_4$ hydrocarbons from line 32.

Among the variations possible in the flow scheme presented in the drawing, is the replacement of the water wash column 10 with an adsorptive type methanol removal zone. The use of such adsorption type systems to remove methanol from the $C_4$ stream discharged from an MTBE plant is described in U.S. Pat. No. 4,371,718. This adsorption can be performed at a temperature of about 40 to about 100 degrees F. (4 to 38 degrees C.) and at a pressure sufficient to maintain liquid phase conditions ranging from about 20 to about 150 psia or more (138 to 1035 kPa). A suitable adsorbent is activated alumina used at a liquid hourly space velocity of about 0.2 to 1.0. A number of known zeolitic materials (molecular sieves) are also suitable. In yet another possible variation of the process flow, as described in U.S. Pat. No. 4,204,077, methanol may be removed from the hydrocarbon mixture by contact with a separate liquid glycol phase. Both of these methods could also be employed in the methanol removal zone 19. A methanol removal zone could also be located in a manner to treat the hydrocarbons before the unreacted hydrocarbons are distilled in the first fractionation zone. The methanol removal zone 19 could also employ a water wash column, although the use of such a water wash column upstream of an alkylation zone is normally not preferred. The operation of the water wash column and the methanol recovery column is described in the references cited herein. A variation in this system is the subject matter of U.S. Pat. No. 4,302,298 which is described as providing a system which removes the methanol by water washing but results in a lower concentration of water in the discharged $C_4$ hydrocarbons.

The $C_4$ feedstream charged to the process through line 32 and/or 28 may contain butadienes. The intended butene-1 product stream normally must contain a fairly low concentration of butadiene to be commercially acceptable. Therefore, it is preferred that, if the feedstream contains butadiene, a selective hydrogenation reaction zone be present at some point within the process flow. For instance, the selective hydrogenation reaction zone could be located in line 32, in line 28, line 4, or line 11. When installed in the feedstream containing lines such as line 4, the selective hydrogenation reaction zone may cause the isomerization of some butene-1 to butene-2. This would decrease the production of butene-1 but would have a beneficial effect on the operation of any downstream motor fuel alkylation zone since butene-2 provides a slightly higher octane number. The operation of the selective hydrogenation zone and the catalyst employed within this zone must therefore be selected with care with consideration being given to the effect of this zone on the butene isomer distribution. Catalyst and processing conditions for selective hydrogenation are well known to those skilled in the art. For instance, hydrogenation for this purpose is described in the article starting at page 51 of the March 1985 edition of *Hydrocarbon Processing*. Suitable catalysts, operating conditions and procedures are described in U.S. Pat. Nos. 3,480,531; 4,551,443; and 4,571,442. The preferred catalyst comprises either palladium or nickel on an alumina support. Preferred is a catalyst containing from about 0.3 to 1.5 weight percent active metal in a sulfided state. Further details on suitable catalysts may be obtained from U.S. Pat. No. 3,472,763 and 4,440,956.

Etherification processes have been constructed and proposed for the production of a variety of ethers. These ethers are themselves useful end products and can be used as feed compounds in processes for producing other valuable chemical compounds. For instance, plans have been announced to produce pure isobutylene for the manufacture of polyisobutylenes and tert-butylphenol by first producing methyl tertiary butyl ether (MTBE) and then cracking the MTBE to yield isobutylene and methanol which is recycled. Large amounts of MTBE are also being produced for use as anti-knock compounds in lead-free gasoline. Etherification processes therefore find utility in both the petrochemical and petroleum refining industries.

The majority of the description of the invention is presented in terms of the reaction of isobutylene with methanol to form MTBE since these are the preferred feed materials and the commercially predominant reaction. However, it is not intended to thereby lessen the scope of the inventive concept which may be applied in the production of other ethers. The inventive concept may therefore be applied in general to the reaction of isobutylene with water-soluble alcohols which preferably have less than four carbon atoms per molecule. The next preferred alcohol after methanol is ethanol but other alcohols such as propanols, ethylene glycol or propylene glycol can also be consumed in the process. The subject process may therefore be employed in the production of a wide variety of ethers other than MTBE including ethyl tertiary butyl ether. Other compounds which may be present in the effluent stream include small amounts of various oxygen-containing reaction by-products, such as dimethyl ether, resulting from side reactions.

The etherification zone may take many different forms but is preferably similar to that described in U.S. Pat. 4,219,678 and shown in the previously cited paper. In this instance the isobutylene, methanol or other feed alcohol, and if desired a recycle stream containing the product ether and methanol are passed into the reaction zone in which they are contacted with an acidic catalyst while maintained at etherification conditions. A wide range of materials is known to be effective as etherification catalysts for the preferred reactants including mineral acids such as sulfuric acid, boron trifluoride, phosphoric acid on kieselguhr, phosphorus-modified zeolites, heteropolyacids, and various sulfonated resins. The use of a sulfonated solid resin catalyst is preferred. These resin-type catalysts include the reaction products of phenol-formaldehyde resins and sulfuric acid and sulfonated polystyrene resins including those crosslinked with divinylbenzene. Further information on suitable etherification catalysts may be obtained by reference to U.S. Pat. Nos. 2,480,940; 2,922,822; and 4,270,929 and the previously cited etherification references.

A broad range of etherification conditions include a superatmospheric pressure sufficient to maintain the reactants as a liquid phase, generally below about 200 psig (1380 k Pag), and a temperature between about 30° and about 100° C. A preferred temperature range is from 50° to 100° C. The reaction rate is normally faster at higher temperatures but conversion is more complete at lower temperatures. High conversion in a moderate volume reaction zone can therefore be obtained if the initial section of the reaction zone, e.g. the first two-thirds, is maintained above 70° C. and the remainder of the reaction zone is maintained below 50° C. This may be accomplished most easily with two reactors. The ratio of feed alcohol to isoolefin should normally be maintained in the broad range of from 1:1 to 2:1. With the preferred reactants good results are achieved if the ratio of methanol to isobutene is between 1.1:1 and 1.5:1. An excess of methanol above that required to achieve satisfactory conversion at good selectivity should be avoided.

It is preferred that the effluent of the etherification reaction zone be passed directly into an intermediate point of the first fractionation column designed and operated to concentrate at least 80 mole percent of the butene-1 present in the effluent into a net overhead stream. Substantially all, that is at least 95 mole percent of the butene-2 must be concentrated into the bottoms stream. The net overhead stream of this column is passed into a water wash zone to recover most of the methanol or other alcohol present in this stream. The bottoms stream of the column receiving the reactor effluent contains the product ether and may contain excess alcohol present in the reaction zone effluent stream. Further details on the separatory method and other aspects of the etherification zone may be obtained from the previously cited references.

A preferred embodiment of the invention may accordingly be characterized as a process for the production of butene-1, which process comprises the steps of passing a mixed $C_4$ charge stream comprising at least about 5.0 mole percent isobutylene and also comprising isobutane, normal butane and butene-1 into an isobutylene consuming reaction zone, and producing an isobutylene depleted mixed $C_4$ process stream which comprises less than about 2.5 mole percent isobutylene; passing the isobutylene depleted mixed $C_4$ process stream and methanol into an etherification reaction zone operated at etherification conditions and producing a reaction zone effluent stream comprising methanol, normal butane, butene-1, isobutane and methyl tertiary butyl ether; separating the reaction zone effluent stream in a first fractionation zone into a net overhead stream comprising methanol, butene-1 and isobutane and a net bottoms stream comprising methyl tertiary butyl ether, normal butane and butene-2, with the net bottoms stream containing at least 10 mole percent hydrocarbons; removing methanol from the net overhead stream; and, separating the thus substantially methanol free net overhead stream in a second fractionation zone into a first process stream which is rich in isobutane and a first product stream which is rich in butene-1, and withdrawing the first product stream from the process.

As used herein, the term "alkylation reaction zone" is intended to indicate a sequence of processing equipment in which the entering reactants are contacted with an alkylation catalyst maintained at alkylation-promoting conditions including one or more reaction vessels and the required equipment for the separation and recovery of the resultant alkylate from process streams recirculated within the reaction zone. It is preferred that the alkylation reaction zone contain no fractionation columns other than any used for catalyst regeneration. The preferred alkylation reaction is the reaction between isobutane and normal butenes to produce high octane $C_8$ hydrocarbons useful as gasoline blending components. Other alkylation reactions can also be performed, but the alkylation zone will be described in terms of the preferred reaction.

The alkylation reaction is preferably promoted by the presence of a mineral acid-catalyst such as hydrofluoric acid, sulfuric acid or phosphoric acid with hydrofluoric acid being preferred. These acids are preferably maintained in a liquid phase containing a minimum of water to reduce corrosion problems. The maximum amount of water normally allowed in HF acid is about 5 wt. %. When fresh HF acid is charged to a plant, it is normally very dry and contains about 0.5 wt. % water or less. The catalyst may also comprise a mixture of a mineral acid and a Friedel-Crafts metal halide promoter such as aluminum chloride, aluminum bromide, boron trifluoride, and other proton donors. The presence of a refractory ether as a component of an HF based catalyst system has also been found to be beneficial as described above. A solid zeolitic catalyst could also be employed if desired.

Alkylation conditions in general include a pressure sufficient to maintain the hydrocarbons and acid in a liquid phase, with a general range being from about 20 to about 500 psig, and a more preferred range being from 100 to about 250 psig. It is preferred that the pressure within the reactant-catalyst contacting vessel be approximately 150 psig and essentially "floats" on the pressure maintained in the downstream product fractionation zone. Although the desired alkylation reaction may be performed at temperatures from below −18° to about 90° C., it is preferred to operate the commercially prevalent isoparaffin-olefin HF alkylation process in the range of from about 10° to about 60° C., with 32° C. being a representative and particularly preferred operating temperature.

Typical operating conditions in the alkyaltion zone include a high ratio of the concentration of the paraffinic or other alkylatable material to the concentration of the olefinic material in order to produce a high quality alkylate by encouraging monoalkylation instead of polymerization. A broad range of this ratio is from about 6 to about 20 with a preferred operating range being from 8 to 12. A second ratio which varies in competing alkylation processes is the ratio of the acid to the hydrocarbons in the total emulsion formed, that is, the ratio in the material charged to the mixing zone or reaction point. This ratio may vary widely from a high of about 10:1 to a low of about 0.5:1, but it is preferred that the subject process be operated at an acid to hydrocarbon ratio of about 2:1.

There are a great number of olefin-isoparaffin alkylation processes known to those skilled in the art. The great majority of these processes will operate within the range of alkylation conditions set out above. They could however have substantial differences in equipment and flow paths used in performing the alkylation. These variations are attempts to obtain optimum quality akylate by varying the method of contacting the monoolefin with the isoparaffin. Since this reaction occurs very rapidly, and also because hydrofluoric acid will catalyze the polymerization of the monoolefin, the standard HF alkylation methods consist of either first admixing acid-free streams of olefin and isoparaffin to form a reactant mixture which is then admixed with the hydrofluoric acid, or an acid-free olefin stream is mixed with an acid-containing isoparaffin stream. In either case, a large number of venturis or mixing nozzles are often utilized to quickly disperse the olefin-containing stream into the acid-containing stream.

The resulting alkylation reaction is very exothermic and it is therefore necessary to provide means to remove the heat of reaction. This is normally done either by providing indirect heat-exchange means within the reacting mixture or by cooling one of the reactant streams, normally the acid stream, prior to passing it to the reaction zone. Mixing the acid and hydrocarbon feed stream results in the formation of an emulsion, and it is preferred that this emulsion be maintained by the continued agitation of the emulsion since this results in the removal of fluorides from the alkylate and the improvement of the octane number of the resulting alkylate. The maintenance of the emulsion is normally effected by its passage through a mixer or soak zone comprising a vessel having a number of internal obstructions which produce substantial turbulence as the emulsion passes through them. The emulsion is then typically fed into some type of settling vessel wherein a gravity separation of the emulsion is performed. The acid phase is removed for recirculation, and the recirculated acid may be cooled to remove the heat of reaction. The hydrocarbon phase removed from the mixer settler is passed into a fractionation column, which preferably operates as an isostripper column. This hydrocarbon phase will comprise mainly alkylate and the excess isoparaffin which was fed to the alkylation zone. Some processes do not utilize a soak zone at all and still others contact the separated hydrocarbon phase with a regenerated high strength acid stream to aid in defluorination. Further details on the design and operation of reaction vessels, the overall operation of the alkylation step, the regeneration of the preferred HF catalyst, etc., may be obtained by reference to the standard reference materials.

The net hydrocarbonaceous effluent stream of the alkyation zone is preferably passed into the isostripper column of the motor fuel alkylation unit. The isostripper recovers the $C_8$ alkylate, other $C_5$-plus hydrocarbons and the MTBE contained in the feed as a net bottoms stream removed as the product of the process. When HF is used as the alkylation catalyst, the bottoms stream contains a small amount of isopentane produced in the alkylation zone. Some propane is also produced in a $C_4$ alkylation process. A representative set of operating conditions for this column includes an overhead vapor temperature of about 60° C. and an overhead pressure of approximately 150 psig. It may contain about 65 actual trays. Preferably, the alkylation zone effluent stream enters the isostripper column at an intermediate point. Sidecut streams are preferably removed above and below the feed point. The upper sidecut carries isobutane which has passed through the alkylation zone. Preferably, this isobutane-rich stream is recycled into the alkylation zone. The lower sidecut stream will normally be rich in normal butane and is withdrawn from the alkylation unit. Since it is a lower sidecut stream, it will contain some product alkylate.

Propane, including any which is present in the feed streams to the alkylation unit, will enter the isostripper as part of the alkylation zone effluent stream. The propane is concentrated into the net overhead vapor of the isostripper. The overhead of the isostripper column will also contain HF and isobutane. This net overhead is preferably passed into a second column referred to in the art as a depropanizer in which the isobutane is recovered as a bottoms product. This isobutane is preferably recycled back to the alkylation zone by admixture into the upper sidecut stream of the isostripper. If there is an excess of isobutane fed to the alkylation unit, this bottoms stream is a good source of high purity isobutane and may be withdrawn from the alkylation zone after being alumina treated. The net overhead of the depropanizer comprises HF and propane and is preferably sent to a third column in which HF is stripped off as an overhead product. The HF may be returned to the alkylation zone and the propane is removed as a net bottoms product and transferred to suitable storage facilities after alumina treatment.

The fractionation performed in the first and second fractionation zones concerns well known components, and the design of columns capable of performing the required separations is believed to be well within the expertise of those of ordinary skill in the art of hydrocarbon conversion process design. Each zone preferably comprises a single trayed column having at least 20 trays. The methanol recovery column and the water wash column may also be of rather straightforward design. The water wash column is preferably a trayed extraction column having over ten trays.

What is claimed is:

1. A process for the production of butene-1, which process comprises the steps of:
    (a) contacting a mixed $C_4$ feedstream comprising isobutylene, isobutane, normal butane, butane-2 and butene-1 and an alcohol with an etherification catalyst maintained at etherification promoting conditions in a reaction zone, and producing a reaction zone effluent stream comprising normal butane, butane-2, butene-1, isobutane and a $C_4$-plus ether;
    (b) separating the reaction zone effluent stream in a first fractionation zone into a net overhead stream comprising butene-1 and isobutane and a net bottoms stream comprising normal butane, butene-2 and the ether, with the net bottoms stream having a hydrocarbon concentration above 10 mole percent;
    (c) recovering the net bottoms stream as a first product stream; and,
    (d) separating the net overhead stream in a second fractionation zone into a second product stream rich in isobutane and a third product stream rich in butene-1.

2. The process of claim 1 further characterized in that the alcohol is methanol and the ether is methyl tertiary butyl ether.

3. The process of claim 1 further characterized in that the feed stream contains less than 5 mole percent isobutylene.

4. The process of claim 3 further characterized in that the feed stream contains less than 2.5 mole percent isobutylene.

5. The process of claim 4 further characterized in that the feed stream is recovered from the effluent of an upstream etherification reactor.

6. The process of claim 5 further characterized in that the first product stream is blended into a motor fuel.

7. The process of claim 6 further characterized in that the net bottoms stream contains over 50 mole percent hydrocarbons.

8. A process for the production of butene-1, which process comprises the steps of:
   (a) passing an isobutylene depleted mixed $C_4$ feedstream comprising isobutylene, isobutane, normal butane, butene-2, butene-1 and an alcohol into an etherification reaction zone operated at etherification conditions and producing a reaction zone effluent stream which comprises the alcohol, normal butane, butene-2, butene-1, isobutane and a $C_4$-plus ether;
   (b) separating the reaction zone effluent stream in a first fractionation zone into a net overhead stream comprising butene-1 and isobutane and a net bottoms stream comprising the ether, normal butane and butene-2, with the concentration of hydrocarbons in the net bottoms stream being greater than 10 mole percent; and,
   (c) separating the net overhead stream in a second fractionation zone into a first process stream which is rich in isobutane and a first product stream which is rich in butene-1, and withdrawing the first product stream from the process.

9. The process of claim 8 further characterized in that the net bottoms stream comprises the alcohol.

10. The process of claim 8 further characterized in that the net bottoms stream is blended into a motor fuel precursor hydrocarbon stream.

11. The process of claim 8 further characterized in that the net overhead stream comprises methanol, and at least a portion of the methanol is removed prior to passage of the net overhead stream into the second fractionation zone.

12. The process of claim 8 further characterized in that at least a first portion of the net bottoms stream is passed into an HF alkylation zone wherein isobutane and butene-2 are reacted to form a $C_8$ alkylate, and the $C_8$ alkylate is recovered in a second product stream.

13. The process of claim 12 further characterized in that a second portion of the net bottoms stream is admixed into the second product stream.

14. The process of claim 12 further characterized in that the ether is methyl tertiary butyl ether.

15. The process of claim 8 further characterized in that the mixed $C_4$ feedstream contains less than 2.5 mole percent isobutylene.

16. The process of claim 15 further characterized in that the mixed $C_4$ feedstream is withdrawn from an isobutylene consuming zone wherein isobutylene is selectively removed from a mixed $C_4$ charge stream containing over about 5.0 mole percent isobutylene.

17. The process of claim 16 further characterized in that the isobutylene depletion zone comprises an etherification reaction zone.

18. The process of claim 16 further characterized in that the isobutylene consuming zone comprises a hydration zone wherein isobutylene is reacted with water to form tertiary butyl alcohol.

19. A process for the production of butene-1, which process comprises the steps of:
   (a) passing a mixed $C_4$ charge-stream comprising at least about 5.0 mole percent isobutylene and also comprising isobutane, normal butane and butene-1 into an isobutylene consuming reaction zone, and producing an isobutylene depleted mixed $C_4$ process stream which comprises less than about 2.5 mole percent isobutylene;
   (b) passing the isobutylene depleted mixed $C_4$ process stream and methanol into an etherification reaction zone operated at etherification conditions and producing a reaction zone effluent stream comprising methanol, normal butane, butene-2, butene-1, isobutane and methyl tertiary butyl ether;
   (c) separating the reaction zone effluent stream in a first fractionation zone into a net overhead stream comprising methanol, butene-1 and isobutane and a net bottoms stream comprising methyl tertiary butyl ether, normal butane and butene-2, with the net bottoms stream containing at least 10 mole percent hydrocarbons;
   (d) removing methanol from the net overhead stream; and,
   (e) separating the thus substantially methanol free net overhead stream in a second fractionation zone into a first process stream which is rich in isobutane and a first product stream which is rich in butene-1, and withdrawing the first product stream from the process.

20. The process of claim 19 further characterized in that at least a first portion of the net bottoms stream is passed into an alkylation zone wherein butene-2 is reacted with isobutane in the presence of liquid phase HF and an alkylate stream comprising a resultant $C_8$ alkylation product is produced.

21. The process of claim 20 further characterized in that a second portion of the net bottoms stream is admixed with the alkylate stream.

22. The process of claim 19 further characterized in that the isobutylene consuming reaction zone is an etherification zone.

23. The process of claim 19 further characterized in that the isobutylene consuming reaction zone is an olefin hydration zone.

24. The process of claim 19 further characterized in that the net bottoms stream contains at least 25 mole percent hydrocarbons.

* * * * *